United States Patent [19]

Cottman

[11] 4,143,076
[45] Mar. 6, 1979

[54] MERCAPTO PHENOLIC AND ALKYLTHIO PHENOLIC ANTIOXIDANTS

[75] Inventor: Kirkwood S. Cottman, Akron, Ohio

[73] Assignee: The Goodyear Tire & Rubber Company, Akron, Ohio

[21] Appl. No.: 879,842

[22] Filed: Feb. 22, 1978

Related U.S. Application Data

[62] Division of Ser. No. 436,751, Jan. 25, 1974, abandoned.

[51] Int. Cl.$^2$ ............................................. C07C 148/00
[52] U.S. Cl. ............................. 260/609 F; 260/671 R; 260/671 M
[58] Field of Search ........... 260/609 F, 671 R, 671 M

[56] References Cited

U.S. PATENT DOCUMENTS

| 3,657,370 | 4/1972 | Hammann et al. ............... 260/671 R |
| 3,714,264 | 1/1973 | Spacht .............................. 260/609 F |

FOREIGN PATENT DOCUMENTS

| 48-34734 | 10/1973 | Japan ..................................... 260/609 F |
| 49-124038 | 11/1974 | Japan ..................................... 260/609 F |

OTHER PUBLICATIONS

C. R. Noller, Chemistry of Organic Compounds, 1965, W. B. Saunders, Co., QD253, N65, p. 555.
E. E. Reid, Organic Chemistry of Bivalent Sulfur, vol. II, 1960, Chemical Publishing Co., QD 412.S1 R4, pp. 27–33.

*Primary Examiner*—Elbert L. Robert
*Assistant Examiner*—Molly C. Eakin
*Attorney, Agent, or Firm*—D. B. Little

[57] ABSTRACT

2-Mercapto phenol and/or 4-mercapto phenol are reacted with a compound selected from olefins, alcohols, and organic halides for example, styrene and isobutylene, to form (hydrocarbyl) thio phenolic antioxidants such as 2,6-di-tert. butyl-4-(tert.butylthio) phenol and 2,6-di($\alpha$-phenylethyl)-4-($\alpha$-phenylethylthio)phenol.

8 Claims, No Drawings

MERCAPTO PHENOLIC AND ALKYLTHIO PHENOLIC ANTIOXIDANTS

This is a division of application Ser. No. 436,751 filed Jan. 25, 1974 now U. S. Pat. No. 4,128,530.

This invention relates to alkylthio phenolic antioxidants and a process for preparing said antioxidants.

U.S. Pat. No. 3,553,163 reveals ring substituted alkylthio phenolic antioxidants. U.S. Pat. No. 3,565,857 reveals alkylthio substituted polynuclear phenolic antioxidants. Canadian Pat. No. 1,290,132 reveals the preparation of ring substituted mercaptophenols. U.S. Pat. No. 3,751,483 reveals the preparation of phenolic thioethers. Those skilled in the art are constantly searching for new and improved antioxidant systems.

It is an object of the present invention to provide new antioxidants for the stabilization of polymers and other materials subject to oxidative degradation as well as to provide stabilized polymers. It is also an object of the present invention to provide the art with a novel method of preparing said antioxidants. Further objects will become apparent as the description of the present invention proceeds.

Some of the objects of the present invention are accomplished by the preparation and use as antioxidants of alkylthio phenolic compounds having the following structural formulae:

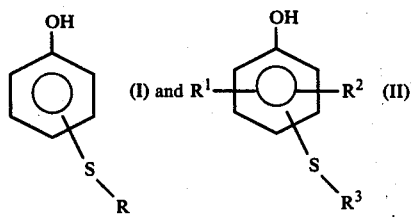

wherein —S—R and —S—$R^3$ are in either an ortho or para position (preferably para) to the hydroxyl group and wherein R and $R^3$ are selected from the group consisting of hydrogen, alkenyl radicals having 2 to 20 carbon atoms, alkyl radicals having 2 to 20 carbon atoms (with the proviso that when $R^3$ is an alkyl radical it contains 4 to 20 carbon atoms), cycloalkyl radicals having 5 to 12 carbon atoms, aralkyl radicals having 7 to 20 carbon atoms and substituted [one or two groups selected from the group consisting of lower alkyls having 1 to 3 carbon atoms, nitro and halo groups (e.g., chloro)] and unsubstituted aryl radicals having 6 to 20 carbon atoms, $R^1$ and $R^2$ are selected from the group of radicals indicated above for R and $R^3$ with the exception that they can also be methyl (i.e., they can be alkyl radicals having 1 to 20 carbon atoms) with the proviso that $R^1$ is never hydrogen and with the further proviso that when $R^3$ is an alkyl radical, neither $R^1$ nor $R^2$ is hydrogen.

Preferably $R^1$ and $R^2$ are in ortho or para positions.

Preferably R and $R^3$ are selected from the group consisting of butyl, hexyl, nonyl, dodecyl, α-phenylethyl, β-phenylethyl, α,α-dimethylbenzyl, cyclohexyl, hexadecyl, methylcyclohexyl and allyl. R preferably can also be ethyl and propyl. The above preferred R and $R^3$ radicals are intended to include normal, secondary and tertiary alkyl radicals. Preferably $R^1$ and $R^2$ are selected from the group consisting of hydrogen, tertiary butyl, tertiary hexyl, nonyl cyclohexyl, α-phenylethyl, α,α-dimethylbenzyl and benzyl.

When a preferred process, as described subsequently herein, is used, neither $R^1$ nor $R^2$ are hydrogen and $R^3$ is a secondary or tertiary alkyl group (preferably tertiary alkyl), e.g., secondary butyl, tertiary butyl, tertiary hexyl, α-phenylethyl, cyclohexyl, and 1,1,3-trimethyl hexyl.

Preferably the —SR and —$SR^3$ radicals are in the para position.

The following compounds illustrate but do not limit the compounds of the present invention.

2-tert.butyl-4-(cyclohexylthio)phenol
b 2,6-ditert.butyl-4-(tert.butylthio)phenol
2-methyl-4-(phenylthio)phenol
2,6-bis(1,1-dimethylbutyl)-4-(1,1-dimethylbutylthio)-phenol
2-α-phenyl ethyl-4-(α-phenylethylthio)phenol
2,6-di-α-phenylethyl-4-(α-phenylethylthio)phenol
2,6-ditert.butyl-4-(dodecylthio)phenol
2,5-dimethyl-4-(4-butylbenzylthio)phenol
2-dimethylbenzyl-4-(hexylthio)phenol
2-α-tolylethyl-4-(tolylthio)phenol
2-propyl-4-(α-phenethylthio)phenol
2-dodecyl-4-(allylthio)phenol
3-methyl-4-(cyclohexylthio)phenol
2,6-ditert.butyl-4-(hexylthio)phenol
2-cyclohexyl-4-(2,4-dimethylcyclohexylthio)phenol
2,6-dihexyl-4-(hexylthio)phenol
2-benzyl-4-(benzylthio)phenol
2-tert.butyl-4-(α-phenethylthio)phenol
2-tert.butyl-4-(allylthio)phenol
2,6-di-tert.butyl-4-(1-methylpropylthio)phenol
2-butyl-4-methyl-6-(tert.hexylthio)phenol
2,4-dibutyl-6-(butylthio)phenol
2,4-di-α-phenylethyl-6-(α-phenylethylthio)phenol
2-cyclohexylthio-4-methyl phenol
2-phenylthio-4-tert.butyl phenol
2- and 4-(ethylthio)phenol
2- and 4-(allylthio)phenol
2- and 4-(propylthio)phenol
2- and 4-(butylthio)phenol
2- and 4-(b 2,4-dimethyltolylthio)phenol
2- and 4-(1,1,3,3-tetramethylbutylthio)phenol
2- and 4-(dodecylthio)phenol
2- and 4-(1-methylpentylthio)phenol
2- and 4-(cyclohexylthio)phenol
2- and 4-(α-phenylethylthio)phenol
2- and 4-(1,1,3-trimethyl-2-pentenethio)phenol
2- and 4-(benzylthio)phenol
2- and 4-(octadecylthio)phenol
2- and 4-(β-phenylethylthio)phenol
2- and 4-(cyclopentylthio)phenol
2- and 4-(cyclopropylthio)phenol
2-and 4-(α,α-dimethylbenzylthio)phenol
2- and 4-nonylthio phenol
2- and 4-(heptylthio)phenol
2- and 4-(nonadecylthio)phenol
2- and 4-(eicosylthio)phenol
2- and 4-(dodecylthio)phenol
2- and 4-(cyclopentylthio)phenol
2- and 4-(methylcyclopentylthio)phenol
2- and 4-(methylpropylthio)phenol Spacht U.S. Pat. No. 3,553,163 took a prior art compound, 4-methylthio phenol, and discovered that by placing a substituent on the ring, he could improve the antioxidant activity. The present invention involves the discovery that increasing the size of the alkyl substituent on the thio group greatly improves the antioxidant activity of the compound whether the compound is ring substituted or unsubstituted.

Other objects of the present invention are accomplished by reacting an alkylating agent selected from the group consisting of olefins, alcohols and organic halides with 2-mercaptophenol and/or 4-mercaptophenol, preferably the latter. This process can be used to produce any of the phenolic antioxidants described herein, both ring-substituted and non-ring substituted, with the exception of those which have both an SH group and ring substituents. The latter compounds can be prepared by the cleavage process described in British Pat. No. 1,290,132.

Another process involves reacting the compound of structural formula (I) with an olefin, alcohol or organic halide.

The reaction between the phenolic compounds and the alkylating agents is carried out according to standard alkylating procedures and involves the standard alkylation techniques common to the art. These techniques are described in U.S. Pat. Nos. 2,181,823; 2,537,337; 3,553,163 and in volume I of *Friedel-Crafts and Related Reactions* edited by George A. Olah, 1963, Interscience Publications, pages 25–91.

The only important considerations regarding the processes about to be described are the reactants used and the molar ratio of one reactant to the other. All other variables such as catalyst, solvent and reaction temperature are immaterial both to the process and to the product prepared thereby. It should be noted that the antioxidants of the present invention are not limited to preparation by the present process.

It has been discovered that when 2-mercapto or 4-mercaptophenol is used, the alkylating agents tend to react at the mercapto site preferentially to a site on the phenolic ring. It has also been discovered that when R is a secondary alkyl group, it is easier to alkylate the phenolic compound in the remaining ortho or para positions. When R is a tertiary alkyl group it is even easier to alkylate in the remaining ortho or para positions. Even the unsubstituted reaction products (i.e., where $R^1$ and $R^2$ are hydrogen) provide very effective stabilization. In addition the ring substituted compounds tend to be less volatile than the unsubstituted compounds.

The olefins used as alkylation agents are monoolefins and contain 2 to 20 carbon atoms. They include open chain olefins such as isobutylene, which can be branched or straight chain as well as cyclic olefins such as cyclohexene. They also include aromatic olefins such as styrene.

The olefins are illustrated by, but not limited to the following compounds.
2-methyl-1-pentene
isobutylene
2-methyl-2-pentene
cyclopentene
1-butene
2,4,4-trimethylpentene-1
1-nonene
2,4-dimethyl-1-heptene
3-nonene
1-hexene
cyclo octene
cyclohexene
propene
2-hexene
methylcyclopentene
vinyl toluene
ethylene
α-methyl styrene
styrene
methyl cyclohexene
1-tetradecene
2-dodecene
1-methyl-1-nonadecene
1-eicosene The reactions between the phenolic reactants and the olefin are acid catalyzed by Friedel-Crafts type catalysts. Friedel-Crafts catalysts and reactions are discussed in volume 1 of *Friedel-Crafts and Related Reactions* edited by George A. Olah, 1963, Interscience Publications, pages 25–91, and in *Encyclopedia of Chemistry*, 3rd. edition, Van Nostraand Reinhold Company, pages 470–471 and include Lewis acid type acidic halides and proton acids. These catalysts are illustrated by metal halides, aluminum chloride, aluminum bromide, aluminum iodide, ferric chloride, zinc chloride, zirconium chloride, boron fluorides (such as boron trifluoride and complexes thereof), acids such as sulfuric acid, aromatic sulfonic acids, phosphoric acid and hydrogen fluoride. Supported phosphoric acid, silica alumina and cation exchange resins are also considered Friedel-Crafts catalysts for the purposes of this invention. The catalyst levels can range from 0.1 gram to 20 grams per 100 grams of the mercapto phenol. Higher catalyst levels can be used but normally offer no advantage. With the more reactive olefins such as styrene, catalyst levels ranging from 0.0 gram to 0.1 gram per 100 grams of mercapto phenol are often adequate.

Free radical catalysts such as benzoyl peroxide or isobutyronitrile may be used. Ultraviolet light can also be used to catalyze the reaction. An inert organic solvent such as benzene, toluene or xylene can be used. Excess olefin can also be used as solvent.

The reaction between the phenolic compound and the olefin can take place at a variety of temperatures, for example, from room temperature to the boiling point of the reactants, although a temperature range of 40° C. to 100° C. is normally preferred. The molar ratio of the phenolic reactant to the olefin is from 1:10 to 10:1, preferably from 1:1 to 1:5.

The alcohols that can be used as alkylating agents are monohydric alcohols having 2 to 20 carbon atoms. The OH group on the alcohol can be attached to a primary, secondary or tertiary carbon atom. The hydrocarbon portion of the alcohol can be a non-cyclic, branched or straight chain radical and can be saturated or unsaturated with one carbon to carbon double bond. The alcohols include those possessing an aryl group with the proviso that the OH group is not directly attached to the aryl radical. Tertiary alcohols are normally much more reactive than secondary alcohols whereas primary alcohols are very difficult to react, benzyl alcohols being the exception. Therefore the tertiary alcohols and benzyl alcohols are preferred. Benzyl alcohols include benzyl alcohol itself as well as substituted benzyl alcohols such as α-phenyl ethanol and 4-methyl benzyl alcohol.

The alcohols are illustrated by, but not limited to the following compounds.
benzyl alcohol
2,4-di-ethyl benzyl alcohol
tertiary butyl alcohol
2-butyl alcohol
tertiary amyl alcohol tertiary hexyl alcohol
α,α-dimethylbenzyl alcohol
para-methyl benzyl alcohol
1,1-dimethyl hexyl alcohol
allyl alcohol
α-phenyl ethyl alcohol The molar ratio of the alcohol to the phenolic reactant is in the same range as described for the olefins. Excess alcohol may be used to function as the solvent for the reaction or an inert organic solvent such as benzene, toluene or xylene can be used. Hydrocarbon solvents such as hexane or pentane may be used in situations where they do not cause solubility problems. Friedel-Crafts type catalysts as described earlier are used to catalyze the reaction. They are used at approximately the same levels as described for the olefinic reactions and at the same reaction temperatures. However, to increase reaction rates, water byproduct can be removed by operating at reflux temperatures. Overall higher levels of catalyst than used with olefins may be necessary depending on the alcohol being used. Normally at least one gram per 100 grams of phenolic reactant is used.

The organic halides that can be used in the reaction with the phenolic reactants have the structural formula RX wherein X is a halide, e.g., a chloro radical and R is selected from the group consisting of alkenyl radicals containing 2 to 20 carbon atoms, cycloalkyl radicals containing 5 to 12 carbon atoms, aralkyl radicals containing 7 to 20 carbon atoms, alkyl radicals containing 2 to 20 carbon atoms, with the exception that when the mercapto group is substituted the alkyl group contains 1 to 20 carbon atoms, and substituted and unsubstituted aryl radicals contain 6 to 20 carbon atoms. As is well known in the art, ring alkylation with the organic halide will not occur with a basic catalyst. Although not all Friedel-Crafts catalysts will result in ring alkylation with the organic halides, some, such as $AlCl_3$ will cause ring alkylation. This is also well known in the art.

Solvents which are well known in alkylation reactions involving organic halides can be used such as benzene, toluene, xylene, carbon tetrachloride, hexane, ethanol and tetrahydrofuran. Catalysts may not be needed for the more reactive halides. To reduce acid corrosion and/or increase reaction rates, bases such as triethylamine, sodium hydroxide, potassium hydroxide and sodium carbonate can be used. Effective catalyst levels include the range from 0.1 mole to 2 moles of base per mole of organic halide. Usually at least one mole of base is used per mole of halide. The reaction temperature may range from room temperature to the boiling point of the reactant and of the solvent.

Since excess organic halide can result in reaction with the OH group of the phenol under basic conditions, it is generally preferred that no more than a slight excess of organic halide be used.

The organic halides are illustrated by, but not limited to the following compounds.
ethyl bromide
ethyl iodide
allyl bromide
benzyl chloride
benzyl bromide
1-hexyl chloride
2-hexyl bromide
α-phenyl ethyl bromide
β-phenyl ethyl bromide
2,4-di-ethyl benzyl bromide
1-nonadecyl bromide
tertiary butyl chloride
allyl chloride
1-butyl chloride
2-butyl chloride
propyl chloride The process of the present invention can also be used to produce antioxidant products where $R^3$ is an alkyl containing 4 to 12 carbon atoms and even 2 to 20 carbon atoms and the phenolic ring contains only one other substituent, i.e., where $R^1$ is hydrogen and $R^2$ is other than hydrogen, e.g., 2-tert.butyl-4-(tert.butylthio)-phenol and 2-α-tolylethyl-4-(tert.butylthio)phenol.

The molar ratio of the alkylating agent to the phenolic reactant can be varied as earlier mentioned. Where a phenolic product containing a substantial amount of phenolic antioxidant free of ring substituents is desired, the molar ratio of alkylating agent to phenolic reactant should be from about 0.25:1 to 1.5:1. Where it is desired to produce a substantial amount of phenolic antioxidant containing only one ring substituent other than the thio substituent, the molar ratio should be from about 1.5:1 to 2.5:1. Where substantial amounts of phenolic antioxidant with two ring substituents other than the alkylthio group are desired, a molar ratio of 2.5:1 to 3.5:1 or even 5:1 or 10:1 and higher should be used. These ratios can vary with the activity of the particular alkylating agent with the particular phenolic reactant. Therefore the above molar ratios are not limiting but merely guidelines for one of ordinary skill in the art.

Some of the more practical compounds of the present invention are those prepared by reacting 4-mercaptophenol with one or more olefins selected from the group consisting of isobutylene, styrene, 2-methyl-1-pentene, diisobutylene, 2,4-dimethyl-1-heptene, α-methyl-styrene, and tetradecene-1. With α-methyl-styrene the reaction between the olefin and the mercaptophenol proceeds more readily if uncatalyzed or if lower levels of Friedel-Crafts catalyst are used or if a free radical catalyst is used. Using the process information recited earlier herein, preferred compounds are:
2,6-di-α-phenethyl-4-(α-phenethylthio)phenol
2-α-phenethyl-4-(α-phenethylthio)phenol
2,6-ditert.butyl-4-(tert.butylthio)phenol
2,6-ditert.butyl-4-(α-phenethylthio)phenol
4-(α-phenethylthio)phenol
4-(tert.butylthio)phenol
2-tert.butyl-4-(α-phenethylthio)-6-α-phenethyl phenol When styrene is used with the mercaptophenol to form a phenethylthio group, the type of catalyst can determine whether the group is an α-phenethylthio or a α-phenethylthio group. If normal amounts of a Friedel-Crafts catalyst is used, the α-phenethyl group will form. If low amounts of the Friedel-Crafts catalyst are used, mixtures of α and β will result. If a free radical catalyst such as AIBN (azobisisobutyronitrile) or no catalyst is used, the β-form will predominate.

It should also be noted that alkylating agents and techniques can be combined. For example, an organic halide or alcohol can be reacted with the mercapto group and the product alkylated with an olefin.

Odor problems with the phenolic products can sometimes be solved by neutralizing or washing the product with dilute KOH or NaOH aqueous solutions.

The following examples illustrate the process of the present invention and the preparation of the phenolic reactants of the present invention. These examples are intended to illustrate but not to limit the practice of the present invention.

EXAMPLE 1

A 4-(hexylthio)phenol was prepared as follows. In a one liter flask equipped with thermometer, stirring rod and water condenser was added 126 grams of 4-mercaptophenol and 7 grams of toluenesulfonic acid. The flask contents were heated to 60° C. and 93 grams of 2-methyl-1-pentene were added over a fifty minute period. The flask contents were neutralized with 9 grams of $Na_2CO_3$ in aqueous solution and decanted. The reaction product was stripped to a pot temperature of 80° C. at 20 millimeters of mercury. It weighed 216 grams.

EXAMPLE 2

Same as Example 1 except 100 grams of 4-mercaptophenol, 7.5 grams of toluenesulfonic acid and 93 grams of diisobutylene were reacted over a forty minute period at 65° C. under nitrogen. The crystallized product was dissolved in benzene and ethyl ether and then water washed. The solvent was removed by stripping. Hexane was added and the product recrystallized from it. The melting point was 78° C. to 89° C. NMR confirmed the product to be 4-(1,1,3,3-tetramethylbutylthio)phenol.

EXAMPLE 3

4-(α-phenethylthio)phenol was prepared as follows. Same as Example 1 except 126 grams of 4-mercaptophenol and 6 grams of toluenesulfonic acid were heated to 60° C. One hundred nine grams of styrene were added over a thirty minute period. The reaction product was neutralized with aqueous $Na_2CO_3$, decanted and stripped to a pot temperature of 80° C. under vacuum. The product weighed 232 grams.

EXAMPLE 4

2-α-phenethyl-4-(α-phenethylthio)phenol was prepared as follows. Same as Example 3 except after adding the styrene at 60° C. the flask contents were heated to 100° C. and an additional 104 grams of styrene were added over a thirty minute period. The flask contents were neutralized with 6 grams of sodium carbonate in aqueous solution, decanted and stripped to a pot temperature of 83° C. at 18 millimeters of mercury. The product weighed 321 grams.

EXAMPLE 5

A 4-(nonylthio)phenol was prepared as follows. 63 Grams of 4-mercaptophenol and 5 grams of toluene sulfonic acid were heated to 60° C. Then 76 grams of nonene (approximately 55 percent 2,4-di-methyl-1-heptene) were added over a 38 minute period. The flask contents were neutralized with 5 grams of $Na_2CO_3$ in aqueous solution, decanted and stripped to a pot temperature of 180° C. at 26 millimeters of mercury. The product weighed 113 grams.

EXAMPLE 6

Sixty-three grams of 4-mercaptophenol, 5 grams of toluene sulfonic acid and 50 milliliters of toluene were heated to 60° C. Twenty-eight grams of isobutylene were added over a ten minute period. The reaction product was neutralized with 5 grams of $Na_2CO_3$ in aqueous solution and decanted. The reaction product was stripped to a pot temperature of 80° C. to remove the volatiles. Petroleum ether was added and the product crystallized to a white fluffy solid. The crude 4-(tert.butylthio)phenol had a melting point of 67° C. to 70° C.

EXAMPLE 7

Same as Example 6 except 56 grams of isobutylene (2 moles) were added. The product was neutralized with aqueous $Na_2CO_3$, decanted and stripped to a pot temperature of 80° C. at 20 millimeters of mercury. It contained a mixture of 4-(tert.butylthio)phenol; 2-tert.butyl-4-(tert.butylthio)phenol and 2,6-di-tert.butyl-4-(tert.butylthio) phenol.

EXAMPLE 8

4-(Ethylthio)phenol was prepared as follows. Sixty grams of 4-mercaptophenol were dissolved in 50 milliliters of ethanol. To the solution was added 27 grams of potassium hydroxide dissolved in 150 milliliters of ethanol. Seventy-four grams of ethyl iodide were added at 20° C. to 32° C. over a thirty minute period. The flask contents were stripped to remove the solvent. Benzene was added and the reaction product was water washed. The reaction product was stripped to remove a trace of the 4-mercaptophenol. The product weighed 66 grams.

EXAMPLE 9

4-(Benzylthio)phenol was prepared as follows. Seventy grams of 4-mercaptophenol, 30 drops of toluene sulfonic acid and 100 milliliters of benzene were placed in a flask. Eighty-three grams of benzyl alcohol were added and the flask contents stirred at reflux for five hours to collect the water formed. A white substance precipitated from solution and was filtered. It was washed with hexane. The substance had a melting point of 96° C. to 98° C., a percent sulfur of 14.4 and a hydroxyl number of 259.

EXAMPLE 10

Sixty-three grams of 4-mercaptophenol, 7 grams of toluene sulfonic acid and 50 milliliters of toluene were reacted as much as possible with isobutylene between 60° C. and 85° C. The reaction product was neutralized with aqueous $Na_2CO_3$ and stripped to a pot temperature of 165° C. under vacuum. A portion of the product was recrystallized from methanol. The melting point was 92° C. to 93° C. The product was characterized as 2,6-ditert.butyl-4-(tert.butylthio)phenol.

EXAMPLE 11

4-(β-phenethylthio)phenol was prepared as follows. Sixty-three grams of 4-mercaptophenol, 100 milliliters of toluene and 57 grams of styrene were heated to 45° C. The reaction was exothermic so the heat was removed. After stirring three hours at 45° C. to 50° C. the reaction product was stripped to a pot temperature of 190° C. at 13 millimeters of mercury. The product weighed 112 grams.

EXAMPLE 12

Fifty grams of 2-tert.butyl-4-methyl-6-mercaptophenol and 5 grams of toluene sulfonic acid were dissolved in 50 milliliters of toluene. Twenty-five grams of 2-methyl-1-pentene was added over a ten minute period and the temperature rose to 41° C. After reacting one hour the product was neutralized with aqueous $Na_2CO_3$. The 2-tert.butyl-4-methyl-6-(tert.hexylthio)phenol was collected at 174° C. to 178° C. at 1 to 2 millimeters of mercury.

EXAMPLE 13

Sixty-three grams of 4-mercaptophenol, 45 grams of 1-hexene, 100 milliliters of benzene and 0.3 gram of AIBN (azobisisobutyronitrile) were heated to 50° C. The mixture was reacted at 50° C. to 65° C. for 65 hours. Gas chromatography then showed 52 percent of what was identified as 4-($\eta$-hexylthio)phenol.

EXAMPLE 14

2,6-di-$\alpha$-phenethyl-4-($\alpha$-phenethylthio)phenol was prepared as follows. One hundred twenty-six grams of 4-mercaptophenol and 6 grams of toluene sulfonic acid were heated to 60° C. Over a 20 minute period 114 grams of styrene was added. The flask contents were heated to 90° C. and 104 grams additional styrene was added over a 30 minute period. At 78° C. to 100° C. an additional 100 grams of styrene was added over a 30 minute period. The product was diluted with 200 milliliters of toluene and neutralized with 3 grams of sodium hydroxide in aqueous solution. The product was stripped to a pot temperature of 110° C. under vacuum. The yield was 416 grams.

Any of the previously recited reactants can be substituted in the previous working examples to prepare phenolic stabilizers.

EXAMPLE 15

Isobutylene was reacted with 0.5 mole of 4-($\eta$-butylthio)phenol, 4-(1-methylpropylthio)phenol and 4-(tert-.butylthio)phenol in separate reactions at 60° C. to 100° C. using 14 grams of toluene sulfonic acid as the catalyst. The relative degree of ease of ortho alkylation around the hydroxyl group was as follows: 4-(tert-.butylthio)phenol ring alkylated quite readily, 4-(1-methylpropylthio)phenol alkylated with much more difficulty and 4-($\eta$-butylthio) phenol gave only slight alkylation.

As shown in Example 15, it is more difficult to ring alkylate the product when the alkyl portion of the alkylthio group is a secondary or normal alkyl group.

The polymers that may be conveniently protected by the compounds described herein are oxidizable vulcanized and unvulcanized polymers susceptible to oxygen degradation, such as natural rubber, balata, gutta percha and oxidizable synthetic polymers including those containing carbon to carbon double bonds, such as rubbery diene polymers, both conjugated and nonconjugated. Representative examples of the synthetic polymers used in the practice of this invention are polychloroprene; homopolymers of a conjugated 1,3-diene such as isoprene and butadiene, and in particular, polyisoprenes and polybutadienes having essentially all of their repeat units combined in a cis-1,4 structure; copolymers of a conjugated 1,3-diene such as isoprene and butadiene with up to 50 percent by weight of at least one copolymerizable monomer including ethylenically unsaturated monomers such as styrene and acrylonitrile; butyl rubber, which is a polymerization product of a major proportion of a monoolefin and a minor proportion of a multiolefin such as butadiene or isoprene; polyurethanes containing carbon to carbon double bonds; and polymers and copolymers of monoolefins containing little or no unsaturation, such as polyethylene, polypropylene, ethylene propylene copolymers and terpolymers of ethylene, propylene and a nonconjugated diene such as dicyclopentadiene, 1,4-hexadiene, ethylidene norbornene and methylene norbornene.

The phenolic antioxidants of this invention may be used with or without other stabilizers, vulcanizing agents, accelerators or other compounding ingredients. In order to effectively stabilize polymers, small proportions of one or more of the phenolic antioxidants in accordance with this invention are added to the polymer in a customary antioxidant amount which may vary somewhat depending upon the type and requirements of the polymers to be produced. The compounds of this invention are useful in protecting polymer in any form, for example, polymer in latex form, unvulcanized polymer and vulcanized polymer.

The method of addition of the antioxidant to the polymer is not critical. It may be added by any of the conventional means such as by adding to a polymer latex, milling on an open mill or by internal mixing. When the stabilizers of this invention are employed to stabilize the cis-1,4 polyisoprene or cis-1,4 polybutadiene rubbers as described above, a convenient method of incorporation consists of adding the stabilizers to the inert organic solvent in which these polymers are normally prepared after the polymerization of the monomers is essentially complete.

Normally from about 0.001 part to about 5.0 parts of the antioxidant by weight based on the weight of the polymer can be used, although the precise amount of these effective stabilizers which is to be employed will depend somewhat on the nature of the polymer and the severity of the deteriorating conditions to which the polymer is to be exposed. In unsaturated polymers such as those made from conjugated dienes, e.g., rubbery butadiene/styrene polymers, the amount of antioxidant necessary is greater than that required by saturated polymers such as polyethylene. It has been found that an effective antioxidant amount of the disclosed stabiilzer in polymers will generally range from about 0.05 part to about 5.0 parts by weight or higher based on 100 parts by weight of the polymer although it is commonly preferred to use from about 0.5 part to about 2.0 parts by weight based on 100 parts by weight of the polymer in most instances where conjugated diene polymers are being stabilized. The above limits are merely guidelines. For example, 2-$\alpha$-phenethyl-4-($\alpha$-phenethylthio)phenol provided similar protection in SBR at the 0.4, 1.0 and 10 parts levels.

The following data illustrates, but does not limit, the use of the compounds of the present invention as antioxidants in various polymers.

A high cis-1,4-polyisoprene (Table I); high cis-1,4-polybutadiene (Table II); and SBR-1006, a rubbery copolymer of butadiene and styrene, (Table III), were all compounded with compounds of the present invention. One part by weight of antioxidant was used in each sample per 100 parts by weight of polymer. The cis-1,4 polybutadiene also contained 1.0 part of triisopropanol amine as a deactivator. Oxygen absorption tests were run as described below. In both the polyisoprene and polybutadiene the time in hours to 1.0 percent $O_2$ absorbed was measured at 90° C. The SBR data was gathered at 100° C.

The cis-1,4-polyisoprene had a cis-1,4 content in excess of 80 percent and the cis-1,4-polybutadiene had a cis-1,4 content in excess of 85 percent.

The oxygen absorption tests were conducted by dissolving in benzene portions of the polymers containing 1.00 part per 100 parts of rubbery polymer of various antioxidant compositions of this invention. The cements so formed were poured onto aluminum foil so as to form a thin film. After drying the weight of rubber was obtained in connection with each sample. Thereafter the foil with the adhering rubber strip was placed in the oxygen absorption apparatus. The time required for each sample to absorb 1.0 percent oxygen was determined and recorded in the following table. This testing procedure is described in further detail in Industrial and Engineering Chemistry, 43, p. 456 (1951) and Industrial and Engineering Chemistry, 45, p. 392 (1953).

Table I

| Cis-1,4 Polyisoprene | | |
|---|---|---|
| Sample | Antioxidant (1.0 part) | Hours to 1.0% Oxygen Absorption at 90° C. |
| 1 | Example 2 | 202 |
| 2 | Example 4 | 282 |
| 3 | Example 10 | 404 |
| 4 | 2,6-ditert.butyl-4-(methylthio)phenol | 125 |

Samples 1, 2 and 3 contained antioxidants of the present invention. Sample 4 did not. The significance of the size of the alkylthio group is quite apparent, the compound in Sample 4 containing a methylthio group and the compounds of Samples 1, 2 and 3 containing octylthio, phenethylthio and butylthio groups respectively.

Table II

| Cis-1,4 Polybutadiene | | |
|---|---|---|
| Sample | Antioxidant (1.0 part) | Hours to 1.0% Oxygen Absorption at 90° C. |
| 5 | Example 2 | 1146 |
| 6 | Example 4 | 1306 |
| 7 | Example 10 | 777 |
| 8 | 4-mercaptophenol | 1118 |
| 9 | 4-(cyclohexylthio)phenol | 496 |
| 10 | 2,6-ditert.butyl-4-(methylthio)phenol | 266 |

Again (Table II) the methylthio substituted compound (Sample 10) was greatly inferior to compounds of the present invention (Samples 5 to 9). The results of Table II also demonstrates that when R is hydrogen (Sample 8) effective protection against degradation is obtained.

Table III

| SBR-1006 | | |
|---|---|---|
| Sample | Antioxidant | Hours to 1.0% Oxygen Absorption at 100° C. |
| 11 | Example 3 | 746 |
| 12 | Example 2 | 882 |
| 13 | Example 4 | 744 |
| 14 | Example 6 | 800 |
| 15 | 4-(nonylthio)phenol | 784 |
| 16 | 4-(cyclohexylthio)phenol | 890 |
| 17 | Example 10 | 645 |
| 18 | 4-mercaptophenol | 455 |
| 19 | 4-(methylthio)phenol | 206 |
| 20 | 2,6-ditert.butyl-4-(methylthio)phenol | 300 |
| 21 | Example 8 | 516 |
| 22 | Example 9 | 385 |
| 23 | Example 6 | 702 |
| 24 | 2,6-di-α-phenethyl-4-(α-phenethylthio)phenol | 692 |
| 25 | 4-mercaptophenol | 339 |
| 26 | 4-(n-butylthio)phenol | 718 |
| 27 | 4-(tetradecylthio)phenol | 739 |
| 28 | 4-(methylthio)phenol | 142 |
| 29 | 4-(allylthio)phenol | 518 |

The data in Table III illustrates again the effectiveness of the compounds of the present invention. The prior art compound 4-(methylthio)phenol (Samples 19 and 28) was inferior in both sets of data.

Compounds of the present invention have been tested in polypropylene and found to provide effective stabilization.

All of the phenolic stabilizers described earlier herein can be substituted in the previous working examples to effectively stabilize the individual polymers.

The phenolic antioxidants of this invention are relatively non-discoloring antioxidants either before or after aging. Often the tinting effect is reduced by ring alkylation and/or the use of larger alkylthio groups.

Several of the phenolic antioxidants were tested in a polypropylene polymer containing a small amount of 2,6-di-tert.butyl-4-methyl phenol using 0.20 part by weight of the antioxidant per 100 parts by weight of the polypropylene. The polymer was aged at 120° C. Failure was taken to be total crazing of the sample. With no additional antioxidant, failure occurred at 8 days. With reaction products formed from 1:1, 2:1 and 3:1 molar ratios of styrene to 4-mercaptophenol, failure occurred at 13, 103 and 149 days respectively. Although some samples failed at 9 or 10 and even 8 days, this was due to the relatively high volatility of the phenolics. Were they to be tested at lower temperatures, they would offer measurable protection.

The polymers stabilized by the compounds of the present invention can be used in their same conventional manner. For example, those that are used as tread stocks for tires or in industrial products such as hoses can still be used in such a manner. In fact, to the extent that the antioxidants improve the performance of these rubbers, they can be used under more severe operating conditions.

In the process described herein it is to be understood that the solvent must not be reactive to any appreciable degree with the catalyst or the reactants (unless of course, it is an alkylating agent itself) and must naturally act as solvent for all of the reactants. For example, pentane is a very poor solvent for 4-mercapto phenol. Such factors are either well known in the art or can be determined by routine experimentation.

In many cases the use of an inert solvent or excess alkylating agent in the process is not necessary. For example, 4-mercapto phenol, which has a melting point of 36° C., can be melted and then alkylated with an olefin such as styrene. In other words, either the 2-mercapto phenol or 4-mercapto phenol when used in liquid form can act as its own solvent for the reaction between the mercapto phenol and the alkylating agent.

It should be noted that in Example 4 the reaction product was a mixture of compounds. However, the major component was 2-α-phenethyl-4-(α-phenethylthio) phenol.

The phenolic compounds of the present invention can be used as stabilizers for organic compounds other than polymers, for example, as stabilizers for gasoline.

When $R^3$—S— is in the para position, preferably $R^1$ and $R^2$ are in the ortho positions.

While certain representative embodiments and details have been shown for the purpose of illustrating the invention, it will be apparent to those skilled in this art that various changes and modifications may be made therein without departing from the spirit or scope of the invention.

I claim:

1. A phenolic compound having the following structural formula:

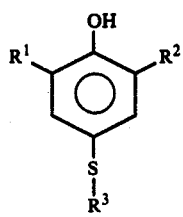

wherein $R^1$ is selected from the group consisting of hydrogen and α-phenyl ethyl, $R^2$ is α-phenyl ethyl and $R^3$ is selected from the group consisting of α-phenyl ethyl and β-phenyl ethyl.

2. The phenolic compound according to claim 1 wherein said compound is selected from the group consisting of 2-α-phenyl ethyl-4-(α-phenyl ethylthio) phenol and 2,6-di-α-phenyl ethyl-4-(α-phenyl ethylthio) phenol.

3. A process of preparing a (hydrocarbyl-thio) phenolic antioxidant having one of the following formulae:

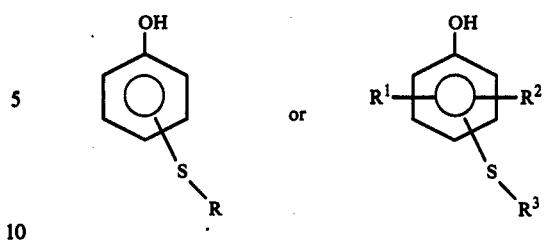

wherein —S—R and —S—$R^3$ are ortho or para to the hydroxyl group; wherein R and $R^3$ are selected from the group consisting of H, alkenyl radicals having 2 to 20 carbon atoms, alkyl radicals having 2 to 20 carbon atoms, with the proviso that when $R^3$ is an alkyl radical it contains 4 to 20 carbon atoms, cycloalkyl radicals having 5 to 12 carbon atoms, aralkyl radicals having 7 to 20 carbon atoms and substituted and unsubstituted aryl radicals having 6 to 20 carbon atoms, $R^1$ and $R^2$ are selected from the group of radicals indicated for R and $R^3$ and methyl, with the proviso that $R^1$ is never hydrogen and with the further proviso that when $R^3$ is an alkyl radical, neither $R^1$ nor $R^2$ is hydrogen; comprising reacting a phenolic compound selected from the group consisting of 2-mercaptophenol and 4-mercaptophenol with a second reactant selected from the group consisting of olefins, alcohols, and organic halides.

4. The process according to claim 3 wherein the second reactant is an olefin.

5. The process according to claim 3 wherein the second reactant is selected from the group consisting of olefins and alcohols and the reaction occurs in the presence of Friedel-Crafts catalyst.

6. The process according to claim 3 wherein the second reactant is an organic halide and the reaction occurs in the presence of a base.

7. The process according to claim 3 wherein the second reactant is styrene.

8. The process according to claim 4 wherein the reaction occurs in the absence of a catalyst.

* * * * *